United States Patent [19]

Eliachar

[11] Patent Number: 4,794,924
[45] Date of Patent: Jan. 3, 1989

[54] LARYNGEAL STENT

[75] Inventor: Isaac Eliachar, Pepper Pike, Ohio

[73] Assignee: The Cleveland Clinic Foundation, Cleveland, Ohio

[21] Appl. No.: 5,143

[22] Filed: Jan. 20, 1987

[51] Int. Cl.$^4$ .............................................. A61M 16/00
[52] U.S. Cl. ..................................... 128/207.16; 623/9
[58] Field of Search ..................... 128/200.26, 207.14, 128/207.15, 207.16, 344; 623/9

[56] References Cited

U.S. PATENT DOCUMENTS

| | | | |
|---|---|---|---|
| 4,044,402 | 8/1977 | Edwards | 623/9 |
| 4,435,853 | 3/1984 | Blom | 623/9 |
| 4,586,505 | 5/1986 | Sisson | 128/344 |

FOREIGN PATENT DOCUMENTS 0078685  5/1983  European Pat. Off. ............... 623/9

Primary Examiner—Steven A. Bratlie
Assistant Examiner—James Prizant
Attorney, Agent, or Firm—D. Peter Hochberg; Mark M. Kusner; Walter C. Danison, Jr.

[57] ABSTRACT

A surgical device for insertion into a living being to support the larynx comprised of an elongated tubular member having a closed, crowed upper end. The device is comprised of a resilient biocompatible polymer material and includes an elongated, narrow aperture through the crowned upper end forming a normally closed valve-like arrangement.

23 Claims, 2 Drawing Sheets

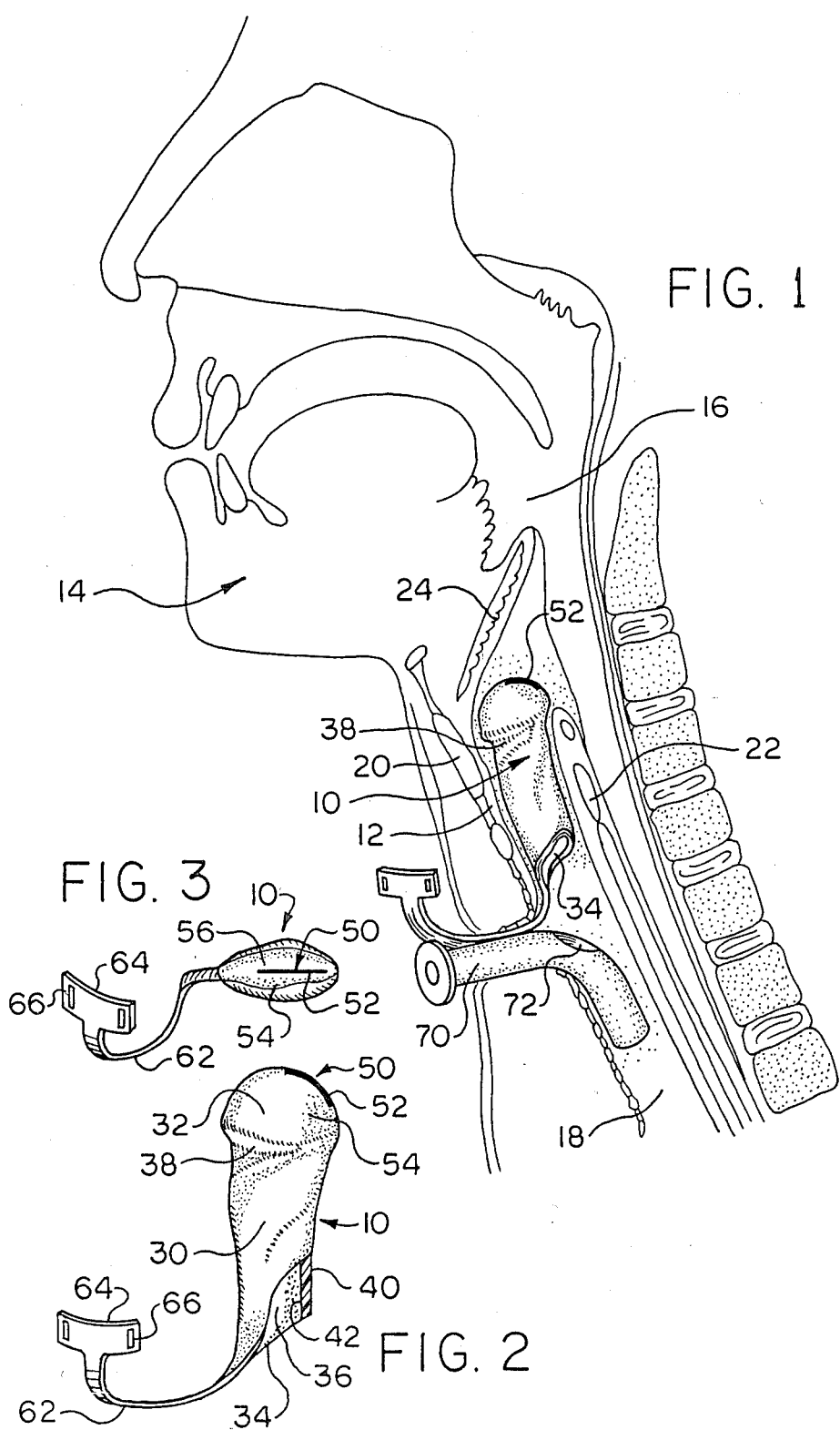

LARYNGEAL STENT

FIELD OF THE INVENTION

The present invention pertains to surgical appliances implanted in living beings to support body structures, and more particularly to a laryngeal stent to support the larynx.

BACKGROUND OF THE INVENTION

Injury or disease which affects the larynx in some situations requires surgical treatment. In extreme cases where resection or reconstruction of the larynx is required, it is conventionally known to use a structure (generally referred to as a "stent") conforming to the internal configuration of the larynx to support the larynx during healing. Laryngeal stents are generally inserted by surgical procedures, but may, in some situations, be inserted through an endoscopic tube. These stents may remain in place for two to four weeks or longer depending on the patient and/or the type of surgery performed. Laryngeal stents known heretofore have been solid, and formed from a biocompatible polymer material When positioned within the larynx, the stent eliminates the ability to speak and more importantly, cuts off air to the lungs. In this respect, a tracheotomy must be performed to enable the patient to breathe, and a T-tube or tracheotomy tube is generally used in conjunction with the stent for as long as the stent is in place in the patient.

A primary function of the larynx is to prevent saliva and other material from entering the lungs via the trachea. Accordingly, stents are dimensioned or formed to conform snuggly to the inner shape of the larynx. Typically, such stents include an enlarged upper portion shaped to generally conform to and engage the surface of the epiglottis. The enlarged upper portion is crowned and tapered downwardly generally along the lines of the aryepiglogtic ligament of the larynx. This upper, crowned portion of the stent is thus operative to divert saliva and other matter towards the esophagus and away from the larynx, trachea and the lungs. From this enlarged upper portion, the stent tapers to a generally cylindrical lower portion which is positioned within the upper portion of the trachea. In the vicinity of the vocal cords, grooves extending from the anterior portion to the posterior portion of the stent are provided on opposite sides thereof to receive the vocal cords.

As set forth above a T-tube or tracheotomy tube is required as long as the stent is in place. In this respect, the T-tube or tracheotomy tube projects through an opening in the tracheal wall to enable the patient to breath. This necessary arrangement, i.e., a stent together with a T-tube or tracheotomy tube, produces several undesirable conditions in the patient. For example, these devices, i.e., the T-tube or tracheotomy tube, create a restriction to normal breathing, and are susceptible to a build-up or a crusting of mucus, dust and moisture on the internal surfaces thereof which further reduces air flow. At instances of high air flow, primarily when the patient coughs, the inability of the tube to transmit increased airflow creates a pressure build-up which acts against the stent and tends to force it upwards. Such violent movement may break sutures and rupture or damage the surgically repaired structure of the trachea and/or larynx. In another respect, the stent-tube arrangement damages the tracheal wall. Normal inhaling and exhaling by the patient produces movement of the tube, which movement abrades the tracheal wall where the tube passes therethrough. In this respect, inhalation and exhalation also produces a similar effect on the stent, thus producing a movement within the larynx which abrades the lining thereof.

Another problem associated with stents known heretofore relates to the comfort of the patient. In this respect, conventionally known stents are generally positioned and maintained in place within the patient by sutures fastened to the stent which extend through the patient's laryngeal cartilages and skin where they are secured by additional sutures. It is also known to secure stents in place with sutures through the nose or mouth. The sutures traumatize the cartilages and skin, which leads to infection, granulation tissue, and scarification, all of which are very uncomfortable for the patient especially when the stent remains in place for prolonged periods of time. Moreover, the stents are solid and relatively rigid, and are a highly irritative and traumatic obstruction within the patient's throat. Perhaps the most important problem associated with stents known heretofore is that they prohibit the patients ability to communicate. In this respect, because the stent necessarily traverses the vocal cords, the patient is unable to produce sound.

The present invention overcomes these and other problems and provides a device that permits venting of high pressure build-ups which may occur below the larynx, enables the patient to produce sound, and prevents seepage of matter into the lungs via the larynx and the trachea. Moreover, the present invention eliminates the need for sutures to secure the stent in place, and provide a more natural, comfortable feeling for the patient.

SUMMARY OF THE INVENTION

In accordance with the present invention there is provided a surgical appliance to support the structure of the larynx in a living being when implanted within the cavity defined by the larynx. The device includes an enlarged, domed upper portion positioned through the glottic region of the larynx, and a narrow lower portion positioned in the subglottic region of the larynx and extending into the trachea. The outer contour of the device generally conforms to the internal configuration of the laryngeal lumen. An internal cavity is formed within the device to define a tubular sleeve-like structure. Valve means are provided to render the internal cavity of the device in communication with the pharyngeal region, which valve means has a normally closed position to effect a sealing of the internal passage and is operative to open upon exhalation of air from the lungs. The device is comprised of a soft, resilient biocompatible polymer material suitable for use in the body of sufficient dimensional stability to support the structure of the larynx.

More specifically, in accordance with a preferred embodiment of the present invention, the device is comprised of a resilient, soft biocompatible silicone material. In a sense, the present invention provides a soft, pliable inner lining or sleeve for the larynx, which lining is of sufficient rigidity to maintain and support the structure of the larynx. A slit through the resilient material forming the enlarged, domed upper portion of the device produces an elongated, narrow aperture having two generally symmetrical flaps which form a normally closed, resilient valve-like arrangement. The valve-like arrangement is operative to open when pressure within the internal cavity of the device increases an amount sufficient to cause yielding separation of the flaps. In this respect, the resilient silicone material provides a one-way directional valve wherein high pressures caused by exhalation or coughing can be vented off through the valve means and thereby prevent damage to the repaired structure and/or sutures in the larynx and/or trachea. In addition, the present invention, being formed of a very soft, non-irritating elastic material that conforms innerlaryngeal contour, is retained in position with no sutures or ties, thereby permitting more natural movement of the supported members of the larynx, and providing a more comfortable feeling for the patient.

In accordance with another aspect of the present invention, there is provided a device as described above including means for locating and securing the device in position within the patient. The locating means is comprised of an elongated band integral with the device extending from the anterior portion thereof. The band is operative to extend through an opening in the tracheal wall and neck to a position external of the patient. The band allows the stent to be positioned within the larynx and secured to the neck without the need for sutures. Moreover, the band extending through the opening in the neck protects the upper tracheal wall from erosion by movement of the curved tracheotomy tube.

In accordance with another aspect of the present invention, there is provided a device as described above which includes means for producing sound.

It is an object of the present invention to provide a laryngeal stent for insertion into the larynx which is operative to enable exhalation from the patient to prevent excessive pressure build-ups in the laryngeal region.

Another object of the present invention is to provide a device as defined above which includes a directional valve which is capable of purging secretions from the lungs, trachea and larynx while at the same time preventing seepage of matter into the lungs via the laryngeal region.

Another object of the present invention is to provide a device as defined above which is operative to prevent disruptive pressure build-ups in a tracheal airway to reduce the likelihood of structural damage to the larynx due to coughing.

Another object of the present invention is to provide a device as defined above which provides a more natural and comfortable feeling for the patient when inserted in the larynx.

Another object of the present invention is to provide a device as described above which is light weight and utilizes a minimum amount of material necessary to structurally support the larynx.

Another object of the present invention is to provide a device as defined above wherein the directional valve means is an integral portion of the stent.

A still further object of the present invention is to provide a device as described above which reduces trauma to the patient and does not require sutures passing through cartilage and skin to maintain its position in the larynx.

Another object of the present invention is to provide a laryngeal stent as described above which is also capable of producing sound.

Another object of the present invention is to provide a device as defined above which includes means to protect the stoma in the tracheal wall from the erosive effect of the tube inserted therethrough.

Another object of the present invention is to provide a laryngeal stent as described above which allows unrestricted movement or removal of any tubular device, such as a tracheotomy tube or T-tube, used in conjunction therewith.

These and other objects and advantages of the invention will become apparent from the following description of a preferred embodiment taken together with the accompanying drawings.

Brief Description of the Drawings

The invention may take physical form in certain parts and arrangement of parts, preferred embodiments of which will be described in detail in this specification and illustrated in the accompanying drawings which are part hereof and wherein:

FIG. 1 is a sectional, partially schematic view of a laryngeal stent illustrating a preferred embodiment of the present invention installed within the larynx of a patient;

FIG. 2 is a partially sectional view illustrating the stent shown in FIG. 1 removed from the patient;

FIG. 3 is a top view of the stent shown in FIG. 2;

DESCRIPTION OF THE PREFERRED EMBODIMENT

Figure 4:
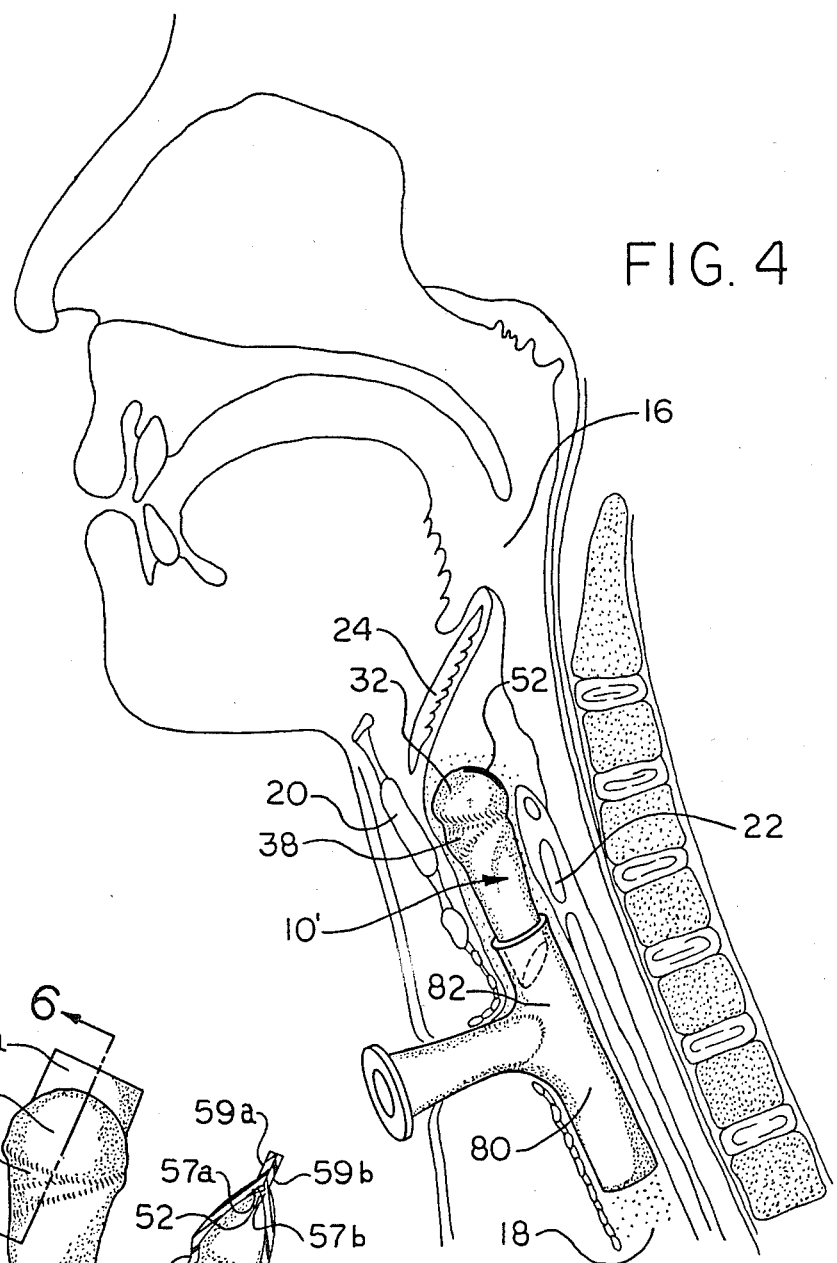
FIG. 4 is a sectional, partially schematic view of a laryngeal stent illustrating a second embodiment of the present invention in combination with a conventionally known T-tube installed in the larynx of a patient.

Referring now to the drawings wherein the showings are for the purpose of illustrating a preferred embodiment of the invention only and not for the purpose of limiting it, FIG. 1 shows a stent 10 in accordance with an embodiment of the present invention installed in the larynx 12 of a patient designated 14. The larynx 12, which is located below the pharynx 16 and above the trachea 18 is comprised of three single cartilages, which are shown in section in FIG. 1, the thyroid 20, the cricoid 22, and the epiglottis 4. The thyroid 20 which is the largest of these cartilages forms the interior part of the larynx and is shaped somewhat like the covers of an open book with the back of the book forming the prominent projection in the anterior neck (Adam's apple). The cricoid cartilage 22 is shaped like a signet ring, with the signet part posterior and the band anterior. The epiglottis 24 is a leaf-like cartilage. The vocal ligaments or cords (not shown) which are comprised of soft tissue covered by mucosa, extend from the thyroid 20 to arytenoid cartilages (not shown) which articulate with the cricoid 22 to move the vocal cords.

Stent 10, best seen in FIGS. 2 and 3, is generally comprised of a tubular, sleeve-like body portion 30 having a closed, rounded or domed upper end 32, and open lower end 34. Tubular body portion 30 and domed upper end 32 define an opening or cavity 36 extending from the open lower end 34. Stent 10 is preferably formed to have a wall thickness which maximizes the space or dimensions of cavity 36. Stent 10 is dimensioned to approximate the laryngeal lumen such that the outer surface 40 of the stent 10 matingly engages with slight contact the surface of the larynx. It should be pointed out that the stents shown in FIGS. 1 and 4 are shown reduced in size relative to the surrounding laryngeal surfaces for the purposes of illustration. An actual stent according to the present invention would be dimensioned to engage such surfaces with the slight contact mentioned. Preferably, stent 10 includes softer regions corresponding to delicate members of the larynx to avoid traumatizing such members. In this respect, certain portions of the wall of stent 10 are thinner than other portions to more easily conform to the contour of these delicate members.

Stent 10 is preferably formed from a soft, resilient, biocompatible polymer material suitable for use in a living body having a surface energy close to the surface energy of the surrounding tissue and dimensional stability sufficient to maintain its shape and to support the larynx. By utilizing a material having a surface energy similar to the surrounding tissue, rejection of the stent by the tissue is less likely to occur, thereby reducing the trauma experienced by the tissue. Preferably, the wall thickness of stent 10 will be the minimum necessary to provide support for the laryngeal structure. It will be appreciated, that the composition of the material used will effect the resiliency, rigidity, strength of the stent, and accordingly will effect the thickness of the wall necessary to support the larynx. In accordance with a preferred embodiment, stent 10 is formed from a resilient, medical grade silicon marketed by the Dow Corning Corporation under the trade designation MDX-4210. The wall of stent 10 is approximately 1/16" thick. The outer surface 40 and inner surface 42 of the stent are preferably smooth to deter adhesion of dust, mucus or moisture; thereon and to minimize abrasion of the laryngeal mucosa. In general, frictional or chemical contact with stent 10 should be non-irritating to the surrounding tissue.

The domed or rounded upper end 32 of stent 10 is enlarged and conforms to the supraglottic region of larynx 12. Depressions 38 transverse to the axis of stent 10 are formed on opposite sides thereof to accommodate the true vocal ligaments therein. As set forth above, the wall thickness of stent 10 in the region of depressions 38 is preferably reduced to receive more easily and with less traumatic impact the vocal cords. These depressions 38 extend from the anterior portion of stent 10 to the posterior portion thereof. (When used herein, anterior shall refer to the region of the stent closest to the front of the neck of the patient, and posterior shall refer to the region of the stent closest to the back of the neck of the patient.) An anterior-to-posterior incision or slit 50 along the upper surface of the rounded or domed end 32 of stent 10 creates an aperture 52 having two side-by-side flaps 54, 56. Aperture 52 and flaps 54, 56 define a unidirectional valve-like arrangement which allows venting of pressure from below the larynx such as when the patient coughs. In this respect, the valve-like arrangement opens slightly when the pressure below the laryngeal region increases in amount sufficient to cause yielding deformation of flaps 54, 56 to open aperture 52. When negative pressure exists below the laryngeal region, such as when the patient inhales, flaps 54, 56 are drawn together to close aperture 52 and prevent matter in the pharynx from being drawn into the lungs via the larynx.

Figures 5, 6:
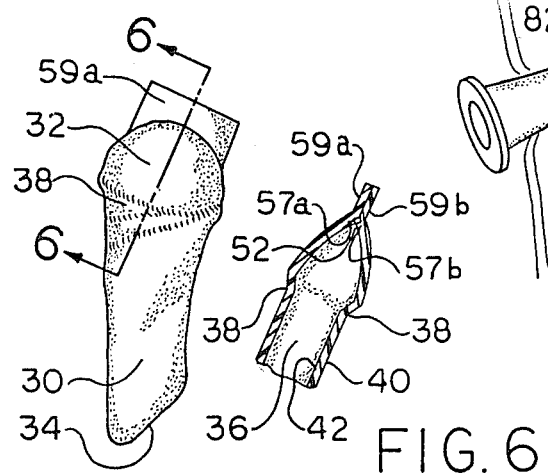
FIG. 5 is a partially sectional view of a stent illustrating an alternate embodiment of the present invention; and, FIG. 6 is a sectional view taken along line 6—6 of FIG. 5.

In addition to providing a means for releasing pressure build-ups below the larynx, stent 10 also provides means for producing sound. In this respect, aperture 52 and flaps 54, 56 may be dimensioned such that when air exhaled from the lungs passes through aperture 52 with sufficient velocity, flaps 54, 56 flutter thereby producing sound. The patient is thus able to communicate, in a crude manner, by controlling the velocity of air flowing through stent 10. It will of course be appreciated that the type of sound produced will depend on the shape and configuration of aperture 52 and flaps 54, 56 as well as the thickness and composition of stent 10. FIGS. 5 and 6 show an alternate embodiment of stent 10 wherein thin, outward extending generally rectangular membranes 59a and 59b are provided adjacent aperture 52 to produce the sound characteristics of the present invention. Membranes 59a and 59b are preferably integrally formed with stent 10 and dimensioned to produce sound when the air flow through aperture 52 exceeds the air flow during the patient's normal breathing. As best seen in FIG. 6, ribs 57a and 57b are provided to effect sealing of aperture 52. It has been found that the configuration of membranes 59a and 59b i.e. their thickness, length, height and shape, affects the tone and pitch of the sound produced. It will thus be appreciated that membranes 59a and 59b can assume different configurations.

Fastening means 60 for positioning stent 10 within the larynxis provided in the form of an elongated band 62 extending from the anterior portion of the lower end 34, as seen in FIG. 2. band 62 is preferably integrally formed with body portion 30 and includes a tab 64 at the free end thereof. Tab 64 includes slotted apertures 66 through which a strap, or the like, may be inserted to secure stent 10 to the neck of the patient.

Referring now to the use of the present invention stent 10 is inserted by endoscopic or surgical procedures into the patient to a position as shown in FIG. 1. As set forth above, a T-tube or tracheotomy tube is used when stents are used in the larynx. FIG. 1 shows stent 10 used in conjunction with a conventionally known curved tracheotomy tube 70. Tube 70 is inserted into the trachea through an artificial opening 72 through the patient's neck and the wall of the trachea. Tracheotomy tube 70 is generally curved for easy insertion into trachea 18 and includes an aperture 72 located along the upper side thereof, which aperture 72 provides a passage from the lungs to the larynx. As set forth above, stent 10 is dimensioned to approximate the form of the laryngeal cavity to engage the inner surface thereof with slight contact. In this respect, the present invention provides a resilient inner sleeve wherein its tubular configuration forces it outwardly against the inner surface of the larynx thereby providing support for the larynx in the form of a soft, pliable lining. Domed end 32 of stent 10 acts as a barrier to prevent food, saliva and other matter from entering the lungs via the trachea. Band 62 extends through opening 72 formed in the neck of the patient wherein a portion of band 62 and tab 64 are external thereto. Band 62 and tab 64 allows stent 10 to be easily positioned and secured to the patient to prevent shifting or movement of the stent while in the patient. More importantly, such an arrangement eliminates the need for sutures to secure the stent in place. This substantially reduces the shock and trauma on the surrounding tissue. In another respect, band 62 protects the anterior superior tracheal wall from erosion which may occur from movement of tracheotomy tube 70 which is used therewith.

Tracheotomy tube 70 may include a one way directional valve (not shown) which would allow air into the lungs via tube 70 but would not permit air to exit via tube 70. Air exhaled from the patient's lungs would then be forced through aperture 72 in tube 70, and be vented through aperture 52 in stent 10. Exhalation through the stent helps purge material from the lungs and maintain the stent 10 free from mucus. In addition, the soft, pliable characteristics of stent 10 enables structural members of the larynx to move naturally, within limits, with less likelihood of lesions and scar tissue forming thereon. Importantly, the thin, contoured wall and resilient nature of the stent enables it to more easily conform to the internal structure of the larynx. In this respect, depressions 38 which receive the vocal cords will yield and conform more readily to the shape of the vocal cords than would a solid stent, and thereby reduce the pressure exerted thereon, which pressure can permanently damage the vocal cords and the patient's ability to speak. Moreover, as mentioned previously, high pressure build-ups produced during patient coughing and talking can be vented-off to prevent rupture or damage to surgically repaired portions of the larynx. The present invention thus eliminates a solid obstruction sutured to the patient's neck with a soft, surface-conforming, resilient sleeve which provides the necessary structural support for the larynx in a manner which enables more natural movement, breathing and phonating by the patient.

FIG. 4 shows an alternate embodiment of the present invention used in conjunction with a conventionally known T-tube 80. Stent 10' shown in FIG. 4 is similar in all respects to stent 10 shown in FIGS. 1-3 with the exception that stent 10' does not include band 62 and tab 64. The open end 34 of stent 10' is wedgingly inserted into the upper branch 82 of T-tube 80. The length of the upper branch 82 of the T-tube 80 may be adjusted by merely cutting the upper branch where appropriate as is conventionally known. The combination shown provides a more stable arrangement which limits or restricts shifting of the T-tube 80 as well as the stent 10' within the patient. It will, of course, be appreciated that stent 10' and T-tube 80 may be integrally formed as a single unit.

The invention has been described with reference to preferred embodiments. Obviously modifications and alterations will occur to others upon the reading and understanding of this specification. For example, although the aforementioned stents have been described as having an anterior-to-posterior extending elongated aperture 52, such aperture could extend from side to side of the stent. It is intended that all such modifications and alternations be included insofar as they come within the scope of the appended claims or the equivalents thereof.

Having thus described the invention, the following is claimed:

1. In a device for supporting the structure of a larynx in a living being when implanted in the internal space defined thereby, said device having an enlarged, upper portion dimensioned to conform to and be positioned in the glottic and supraglottic region of the larynx, and a tapered lower portion dimensioned to conform to and be positioned in the subglottic region of the larynx and the improvement comprising:

an internal cavity within said device extending from said lower portion into said upper portion and communicating with the tracheal airway; and, valve means in said upper portion for rendering the pharyngeal region in communication with said cavity, said valve means being operable to open upon exhalation of air from the lungs and having a normally closed position to effect sealing of said cavity and tracheal airway from deleterious liquid or solid matter in the pharynx about the larynx.

2. A device as defined in claim 1 wherein said valve means comprises an anterior-to-posterior slit in the upper portion of the device, said slit forming a normally closed, resilient valve-like arrangement operative to open when pressure within said internal opening in said device increases an amount sufficient to cause said valve to yieldingly separate.

3. A device as defined in claim 2 wherein said device is comprised of a resilient silicon material.

4. A device as defined in claim 2 wherein said device is generally hollow and defines a wall having a thickness which varies relative to predetermined portions of the larynx.

5. A device as defined in claim 1 further comprising means associated with said valve means operative to produce sound when air is passed through said valve means from said cavity into said pharyngeal region.

6. A device as defined in claim 1 further comprising an elongated strap extending longitudinally from the anterior, lower portion of said device, said strap dimensioned to project through a stoma for a tube in the trachea wall, and to be secured to the neck portion of the patient.

7. A device as defined in claim 1 wherein said device is comprised of a resilient plastic material and said valve means comprises a region of reduced wall thickness on said upper portion, said region having an outward curvature and a slit extending therethrough, said slit forming a normally-closed, resilient valve-like arrangement operative to open hen pressure within said internal opening in said device increases an amount sufficient to cause yieldingly deformation of said region.

8. An appliance for insertion into a living being to support the larynx, said appliance comprised of:

an elongated, generally tubular body portion, an outwardly, generally rounded end portion integral with said body portion enclosing one end thereof, an outer surface substantially conforming to the inner configuration of the larynx including transverse depressions to accept the normal anatomy of the vocal cords, said appliance being formed of a resilient biocompatible polymer material and being dimensioned to be received longitudinally within the passage defined by the trachea and larynx with said end portion in the pharyngeal passage, an internal cavity defined by said body portion and said end portion, and an elongated, narrow aperture through said end portion, said aperture forming a normally closed valve-like arrangement operable to open when the pressure within said cavity is sufficient to cause yielding deformation of said resilient material adjacent said aperture.

9. An appliance as defined in claim 8 wherein said body portion and end portion define a wall of generally uniform thickness.

10. An appliance as defined in claim 8 wherein said member is dimensioned to conform with slight contact to the inner surface of the larynx.

11. An appliance as defined in claim 8 wherein said elongated narrow aperture is an incision through said crowned upper end.

12. An appliance as defined in claim 11 wherein said incision extend from the anterior to the posterior of said crowned, upper end.

13. An appliance as defined in claim 8 wherein said device is comprised of a silicon material.

14. An appliance as defined in claim 8 further comprised of means for positioning and securing said appliance in the larynx.

15. An appliance as defined in claim 14 wherein said means for positioning and securing is comprised of an elongated band extending from the lower, anterior end of said tubular member.

16. An appliance as defined in claim 15 wherein said band is integrally formed with said tubular member.

17. An appliance as defined in claim 8 further comprised of means for producing sound.

18. An appliance as defined in claim 17 wherein said means for producing sound is comprised of a vibrating membrane.

19. An appliance for insertion into a living being to support the larynx, said appliance comprised of:
an elongated tubular member of a resilient biocompatible polymer material having a closed, crowned upper end, and a wall of predetermined thickness, said member dimensioned to be positioned axially within the passage defined by said larynx with said crowned end positioned in the pharyngeal cavity wherein said wall engages the inner surface of the larynx, supports the structure thereof, and maintains an opening therethrough, said upper end including means for producing sound when air from the lungs passes through said opening.

20. An appliance as defined in claim 19 wherein said means for producing sound is comprised of an elongated narrow aperture through said crowned upper end defining two side-by-side sound producing members, said members operative to flutter and produce sound when air of a predetermined velocity moves thereover.

21. An appliance as defined in claim 19 further comprising an elongated narrow aperture through said crowned upper end forming a normally close valve-like arrangement, said means for producing sound comprised of a thin elastic membrane is provided adjacent said aperture, said membrane operative to produce sound when air flows thereover.

22. An elongated sleeve-like device of a resilient biocompatible polymer material for insertion into the larynx and trachea of a living being to support the anatomical structures of the larynx from within, said device including:
an elongated tubular body portion of generally circular cross-section adapted to be snugly positioned within the passages defined by the larynx, said body portion being dimensioned lengthwise such that one end thereof is positioned in the pharyngeal cavity and the other end thereof is positioned below the larynx in the treachea, said body portion having a generally uniform wall thickness and an outer diameter dimensioned slightly larger than said passage defined by the larynx wherein said resilient material forming said body portion generally conforms with the inner surface of the larynx and exerts a slight outward force thereon to support the structure of the larynx and to maintain an opening therethrough,
an outwardly rounded portion at said one end of said tubular portion, said rounded portion being integral to said body portion and defining a wall of predetermined thickness, and
valve means in said rounded portion having a normally closed position wherein said opening within said device is sealed from said pharyngeal cavity, said valve means being operable to open when pressure within said opening is greater than pressure in said pharyngeal cavity.

23. A device as defined in claim 22 further comprising means for producing sounds when air moves through said valve means above a certain velocity.

* * * * *